United States Patent [19]
Dandekar et al.

[11] Patent Number: 6,069,289
[45] Date of Patent: May 30, 2000

[54] PROCESS FOR SEPARATING AND RECOVERING MULTIMETHYL-BRANCHED ALKANES

[75] Inventors: Hemant W. Dandekar, Roselle; Gregory A. Funk, Carol Stream; Herman A. Zinnen, Evanston, all of Ill.

[73] Assignee: UOP LLC, Des Plaines, Ill.

[21] Appl. No.: 09/144,229

[22] Filed: Aug. 31, 1998

[51] Int. Cl.[7] .................................................. C07C 7/12
[52] U.S. Cl. ......................... 585/820; 585/734; 585/738; 585/826; 585/829
[58] Field of Search .................... 585/738, 734, 585/826, 829

[56] References Cited

U.S. PATENT DOCUMENTS

| | | | |
|---|---|---|---|
| 3,122,494 | 2/1964 | Brown et al. | 208/63 |
| 3,205,166 | 9/1965 | Ludlow et al. | 208/310 |
| 3,696,107 | 10/1972 | Neuzil | 260/674 SA |
| 3,723,302 | 3/1973 | Pharis et al. | 208/310 |
| 4,006,197 | 2/1977 | Bieser | 260/676 MS |
| 4,031,151 | 6/1977 | Healy et al. | 260/666 A |
| 4,031,155 | 6/1977 | Healy et al. | 260/674 SA |
| 4,031,156 | 6/1977 | Geissler et al. | 260/674 SA |
| 4,036,745 | 7/1977 | Broughton | 208/310 Z |
| 4,783,574 | 11/1988 | Barnes | 585/738 |
| 4,804,802 | 2/1989 | Evans et al. | 585/734 |
| 4,855,529 | 8/1989 | Stem et al. | 585/737 |
| 5,026,951 | 6/1991 | Schmidt et al. | 585/738 |
| 5,043,525 | 8/1991 | Haizmann et al. | 585/737 |
| 5,059,741 | 10/1991 | Foley | 585/734 |
| 5,146,037 | 9/1992 | Zarchy et al. | 585/738 |
| 5,245,102 | 9/1993 | Zarchy et al. | 585/738 |
| 5,405,534 | 4/1995 | Ishida et al. | 210/662 |
| 5,510,564 | 4/1996 | Raghuram et al. | 585/822 |
| 5,530,172 | 6/1996 | Funk et al. | 585/736 |
| 5,530,173 | 6/1996 | Funk et al. | 585/737 |
| 5,744,683 | 4/1998 | Dandekar et al. | 585/736 |
| 5,744,684 | 4/1998 | Zinnen et al. | 585/737 |
| 5,763,730 | 6/1998 | Dandekar et al. | 585/736 |
| 5,770,783 | 6/1998 | Zinnen et al. | 585/738 |

*Primary Examiner*—Helane Myers
*Attorney, Agent, or Firm*—Thomas K. McBridge; Frank S. Molinaro; Maryann Maas

[57] ABSTRACT

A process to separate multimethyl-branched alkanes from a mixture of multimethyl-branched alkanes, monomethyl-branched alkanes, and normal alkanes has been developed. The mixture is introduced to a simulated moving bed of solid adsorbent particles having the selectivity normal alkanes>monomethyl-branched alkanes>multimethyl-branched alkanes. The adsorbent may be silicalite, ferrierite, zeolite Beta, MAPO-31, SAPO-31, SAPO-11, zeolite X ion exchanged with alkaline cations, alkaline earth cations, or a mixture thereof, and zeolite Y ion exchanged with alkaline cations, alkaline earth cations, or a mixture thereof. A raffinate stream enriched in multimethyl-branched alkanes is removed from the simulated moving bed. The monomethyl-branched alkanes are desorbed from the solid adsorbent particles using a first desorbent capable of desorbing the monomethyl-branched alkanes but incapable of desorbing the normal alkanes and first extract stream enriched in the desorbed monomethyl-branched alkanes is removed from the simulated moving bed. The normal alkanes are desorbed from the solid adsorbent particles using a second desorbent, and a second extract stream enriched in the desorbed normal alkanes is removed from the simulated moving bed. The process may be incorporated into an isomerization flowscheme.

12 Claims, 2 Drawing Sheets

PROCESS FOR SEPARATING AND RECOVERING MULTIMETHYL-BRANCHED ALKANES

BACKGROUND OF THE INVENTION

Isomerization processes generate a mixture of isomers that usually require separation and recycle of the non-isomerized components. For example, the effluent of a paraffin isomerization reactor may contain normal alkanes, monomethyl-branched alkanes, ethyl-pentane, and multimethyl-branched alkanes. Traditionally, only the normal alkanes would be separated from the mixture by adsorption and recycled to the isomerization reactor; see U.S. Pat. No. 5,043,525, and any monomethyl-branched alkanes would be collected with the multimethyl-branched alkanes as product. However, it is the multimethyl-branched alkanes that are the most desired and have the highest octane number components. Therefore, the more efficient approach would be to adsorptively separate only the multimethyl-branched alkanes as product and recycle the normal and the monomethyl-branched alkanes to the isomerization reactor. However, with many of the adsorbents available today this separation is extremely difficult because the adsorbents exhibit only a slightly greater selectivity for the monomethyl-branched alkanes as compared to the multimethyl-branched alkanes, while the selectivity for the normal alkanes is greater relative to the monomethyl- and multimethyl-branched alkanes. Desorbents capable of fully desorbing the normal alkanes also prevent the monomethyl-branched alkanes from being adsorbed and separated from the multimethyl-branched alkanes. The invention described herein provides a process for separating the multimethyl-branched alkanes from an isomerization reactor effluent using a single adsorbent contained in a simulated moving bed and two desorbents of differing desorbent capability.

Others have used two desorbents in simulated moving bed adsorptive separations. U.S. Pat. Nos. 4,031,151, 4,031,156, and 4,031,155 disclose using a stronger desorbent in the desorption zone and a weaker desorbent in the rectification zone. The improvement provided by these disclosures center on effecting the desorption of the weakly adsorbed raffinate components in the rectification zone so that when the rectification zone becomes the desorption zone in a succeeding cycle of operation, only the desired sorbate component remains adsorbed.

U.S. Pat. Nos. 4,036,745 and 4,006,197 describe using a first desorbent to desorb surface adsorbed aromatic contaminates from the adsorbent and to sweep the contaminates out of the simulated moving bed and then a second desorbent to remove and collect the desired component from the pores of the adsorbent. U.S. Pat. No. 3,723,302 discloses a two-desorbent system for the removal of contaminants in a process for separating olefins from paraffins. The first desorbent causes contaminants to be desorbed and removed in a first extract stream and the second desorbent is used to desorb the product which is removed in a second extract stream.

U.S. Pat. No. 3,696,107 discloses a process for separating para-xylene from a mixture of $C_8$ aromatics where a first desorbent is used to desorb para-xylene from the adsorbent and a second desorbent is used to sweep the desorbed para-xylene from the interstitial void spaces between the adsorbent particles. U.S. Pat. No. 5,510,564 discloses a process for separating normal paraffins and isoparaffins along with the removal of aromatics. Paraffins and the aromatics are sorbed by a sorbate and isoparaffins are collected. The paraffins and aromatics are desorbed using a first desorbent and are contacted with a second sorbate which sorbs the aromatics. The normal paraffins are flushed or purged from the interstitial void spaces between the second sorbate particles and the adsorbed aromatics are then desorbed.

U.S. Pat. No. 3,205,166 discloses a separation process producing a normal aliphatic hydrocarbon portion, an aromatic component portion, and a branched chain and cyclo-paraffinic hydrocarbon portion. The process uses a mixture of adsorbents, one selective for normal aliphatic components and the other selective for aromatic components. A first desorbent is used to desorb the normal aliphatic components from the first adsorbent, and a second desorbent is used to desorb the aromatic components from the second adsorbent. Multiple adsorbents are also disclosed in U.S. Pat. No. 5,405,534 describing an apparatus for separating a three-component mixture.

U.S. Pat. Nos. 5,530,173 and 5,530,172 describe concurrent isomerization with separation of reactants and products using a simulated moving bed containing both catalyst and adsorbent. An embodiment disclosed is one where the desorbent used is itself isomerized thereby yielding two desorbents within the simulated moving bed.

Using two desorbents of different desporptive capacities enables the present invention to efficiently accomplish a difficult separation using a simulated moving adsorbent bed. A single desorbent having sufficient desorption capacity to desorb the normal alkanes would prevent separation of the monomethyl-branched alkanes from the multimethyl-branched alkanes. A single desorbent of low enough desorption capacity to effect the separation of the monomethyl-branched alkanes from the multimethyl-branched alkanes would be required in such high quantity to desorb the normal alkanes so as to make its use impractical.

SUMMARY OF THE INVENTION

The purpose of the invention is to separate multimethyl-branched alkanes from a mixture of multimethyl-branched alkanes, monomethyl-branched alkanes, and normal alkanes. The mixture is introduced into a simulated moving bed of solid adsorbent particles having the selectivity for normal alkanes>monomethyl-branched alkanes>multimethyl-branched alkanes. The adsorbent particles may be silicalite, ferrierite, zeolite Beta, MAPO-31, SAPO-31, SAPO-11, zeolite X ion exchanged with alkaline cations, alkaline earth cations, or a mixture thereof, and zeolite Y ion exchanged with alkaline cations, alkaline earth cations, or a mixture thereof. A raffinate stream enriched in multimethyl-branched alkanes is removed from the simulated moving bed. The monomethyl-branched alkanes are desorbed from the solid adsorbent particles using a first desorbent capable of desorbing the monomethyl-branched alkanes but incapable of desorbing the normal alkanes, and a first extract stream enriched in the desorbed monomethyl-branched alkanes is removed from the simulated moving bed. The normal alkanes are desorbed from the solid adsorbent particles using a second desorbent, and a second extract stream enriched in the desorbed normal alkanes is removed from the simulated moving bed.

Another purpose of the invention is one where multimethyl-branched alkanes are produced through the catalytic isomerization of a feedstock containing $C_5$ alkanes along with $C_6$ and/or $C_7$ alkanes and then separated from other isomerization products and reactants. The isomerization of the feedstock forms a mixture of normal, monomethyl-branched, and multimethyl-branched alkanes which is separated into at least three portions: a portion enriched in 2-methylbutane; a portion enriched in normal pentane; and a portion enriched in alkanes having 6 or more carbon atoms. The portion enriched in alkanes having 6 or more carbon atoms is continuously introduced to a simulated moving bed of solid adsorbent particles having the selectivity for normal alkanes>monomethyl-branched alkanes>multimethyl-branched alkanes. The adsorbent may be silicalite, ferrierite, zeolite Beta, MAPO-31, SAPO-31, SAPO-11, zeolite X ion exchanged with alkaline cations, alkaline earth cations, or a mixture thereof, and zeolite Y ion exchanged with alkaline cations, alkaline earth cations, or a mixture thereof. A raffinate stream enriched in multimethyl-branched alkanes is removed from the simulated moving bed. The monomethyl-branched alkanes are desorbed using the portion enriched in 2-methylbutane and a first extract stream enriched in desorbed monomethyl-branched alkanes is removed from the simulated moving bed. The normal alkanes are desorbed using the portion enriched in normal pentane and a second extract stream enriched in normal alkanes is removed from the simulated moving bed.

Figure 1:
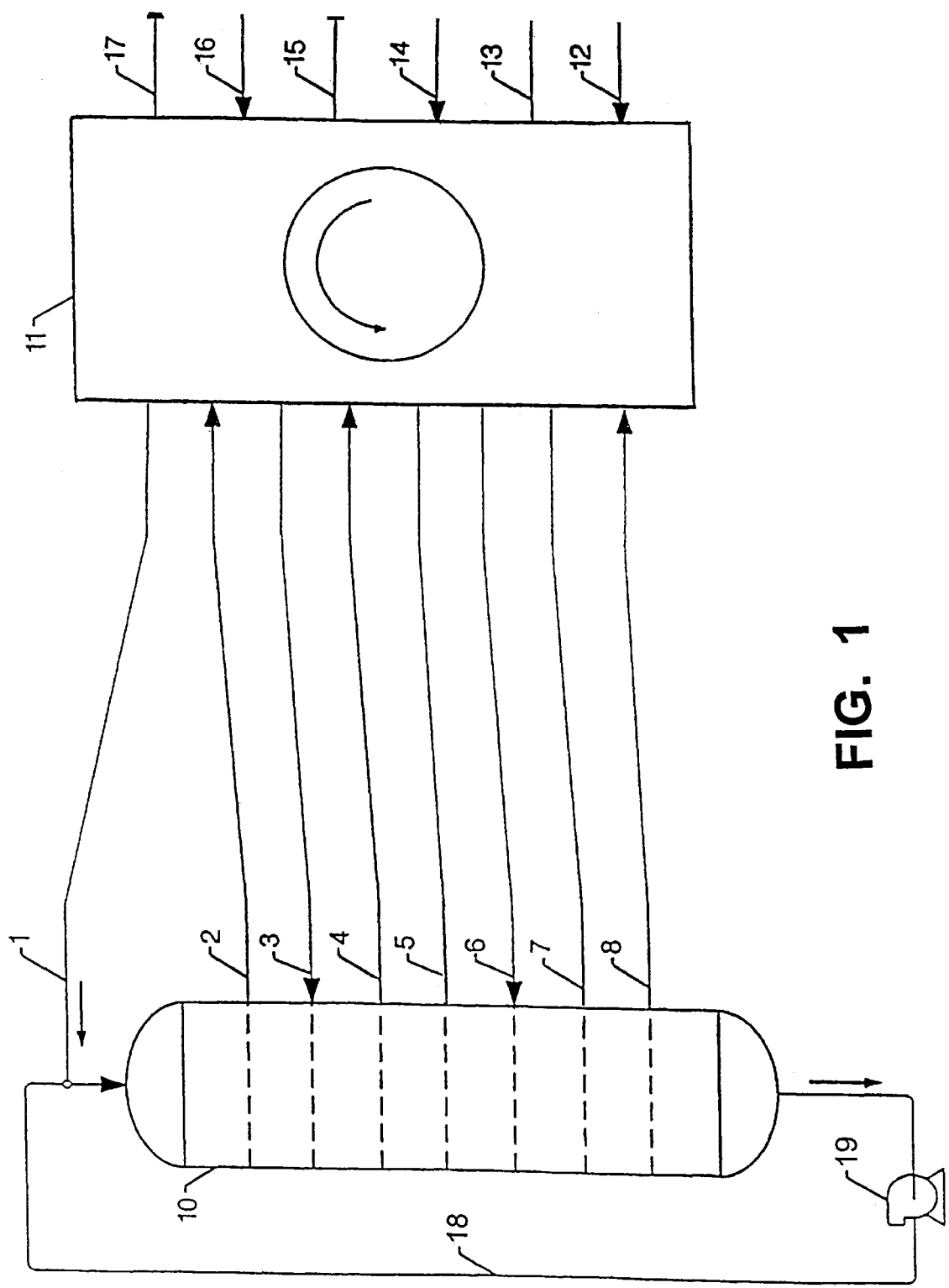
FIG. 1 is a schematic representation of a simulated moving adsorbent bed separation process modified and operated in accordance with the process of the present invention.

The drawings have been simplified by the deletion of a large number of pieces of apparatus customarily employed on processes of this nature which are not specifically required to illustrate the performance of the present invention.

DETAILED DESCRIPTION OF THE INVENTION

The most valuable products of an alkane isomerization process are generally the multimethyl-branched alkanes due to their superior octane number. It is desirable to recycle low octane number normal and monomethyl-branched alkanes to the isomerization reactor for further isomerization. However, it has been difficult to separate the monomethyl-branched alkanes from the multimethyl-branched alkanes using conventional techniques. The present invention overcomes this deficiency and provides a process for separating multimethyl-branched alkanes from a mixture of multimethyl-branched alkanes, monomethyl-branched alkanes, and normal alkanes using a simulated moving bed of solid adsorbent particles, two desorbent streams of different composition, two extract streams, and a raffinate stream.

The solid adsorbent particles are arranged in the form of a simulated moving bed where the bed is held stationary, and the locations at which the various streams enter and leave the bed are periodically moved. The bed itself is usually a succession of fixed sub-beds, and different isomerization reactions may require differing numbers of sub-beds. The most commonly used range is from about 5 sub-beds to about 24 sub-beds with the preferred range being from about 6 to about 24 sub-beds, and the most preferred range being from about 8 to about 24 sub-beds. The sub-beds are housed in individual interconnected chambers, and each chamber is equipped with an inlet and an outlet line.

The shift in the locations of input and output streams in the direction of the fluid flow through the bed simulates the movement of the solid bed in the opposite direction. Commercially, moving the locations of the input and output streams may be accomplished by a variety of fluid-directing devices such as rotary valves or a network of two-position or multi-position valves which work in conjunction with the inlet and outlet lines of the sub-beds. The fluid-directing device accomplishes moving the locations of the input and output streams through first directing the streams to the appropriate inlet or outlet lines of the sub-beds. After a specified time period called the step time, the fluid-directing device advances one index and redirects the streams to the inlet or outlet line immediately adjacent and downstream of the previously used inlet or outlet line. Each advancement of the fluid-directing device to a new position is generally called a step, and the completion of all the valve steps is called a cycle. The step time is uniform for each step in a cycle, and the cycle time ranges generally from about 5 minutes to about 1 hour.

The operating conditions of the simulated moving bed will depend upon the adsorbent selected. Typical operating temperatures for the process are about 100° C. to about 500° C., preferably from about 150° C. to about 250° C. Typical operating pressures for the process are about $2.5 \times 10^5$ to about $7.5 \times 10^6$ N/m² preferably from about $7.5 \times 10^5$ to about $1.825 \times 10^6$ N/m². The process conditions are typically set so that all the streams are in the gas phase.

The mixture to be separated will contain a variety of alkanes including multimethyl-branched alkanes, monomethyl-branched alkanes, and normal alkanes. The mixture will most likely contain $C_6$ and/or $C_7$ alkanes. The mixture may also contain $C_5$ alkanes. Typical alkanes include normal pentane, 2-methylbutane, normal hexane, 2-methylpentane, 3-methylpentane, normal heptane, 2-methylhexane, 3-methylhexane, 2,2-dimethylpropane, 2,3-dimethylbutane, 2,2-dimethylbutane, 2,2-dimethylpentane, 3,3-dimethylpentane, 2,3-dimethylpentane, 2,4-dimethylpentane, 2,2,3-trimethylbutane, and 3-ethyl-pentane.

The solid adsorbent particles chosen for use in the simulated moving bed must have a selectivity for the mixture components as follows: normal alkanes>monomethyl-branched alkanes>multimethyl-branched alkanes. Suitable adsorbents include silicalite, ferrierite, zeolite Beta, MAPO-31, SAPO-31, SAPO-11 zeolite X ion exchanged with alkaline cations, alkaline earth cations, or a mixture thereof, and zeolite Y ion exchanged with alkaline cations, alkaline earth cations, or a mixture thereof. The preferred adsorbent is silicalite. Depending upon the application, mixtures of suitable adsorbents may be employed.

The mixture of alkanes to be separated is introduced to the simulated moving bed. Any multimethyl-branched alkanes are relatively unabsorbed by the adsorbent and are carried with the fluid flow through a first zone (zone I) of the simulated moving bed and removed in a raffinate stream. The adsorption of normal and monomethyl-branched alkanes by the adsorbent is also occurring in zone I. The adsorbed normal and monomethyl-branched alkanes are carried through a second zone of the simulated moving bed (zone II) with the simulated movement of the adsorbent to remove them from the multimethyl-branched alkanes, and the adsorbed components enter a third zone of the simulated moving bed (zone III).

In zone III, only the monomethyl-branched alkanes are desorbed from the solid adsorbent particles using a first desorbent. In a reasonable quantity, the first desorbent must be capable of desorbing the monomethyl-branched alkanes but incapable of desorbing the normal alkanes. In general, suitable desorbents for zone III include those enriched in monomethyl-branched alkanes or butanes including 2-methylbutane, isobutane, and normal butane. A preferred desorbent is one enriched in 2-methylbutane. The desorbed monomethyl-alkanes are removed from zone III as a mixture with desorbent in a first extract stream. The normal alkanes remain adsorbed on the solid adsorbent particles and are carried with the simulated movement of the solids through zone IV of the simulated moving bed where any residual monomethyl-branched alkanes are desorbed.

The adsorbed normal alkanes enter zone V of the simulated moving bed where they are completely desorbed using a second desorbent. A reasonable quantity of the second desorbent must be capable of fully desorbing the adsorbed normal alkanes. The second desorbent is preferably enriched in normal alkanes and most preferably enriched in normal pentane. Some monomethyl-branched alkanes may also be present in the second desorbent, e.g., the second desorbent may be a mixture of mainly normal pentane with some 2-methylbutane. The desorbed normal alkanes are removed from zone V of the simulated moving bed as a mixture with a second desorbent in a second extract stream. Note that if only the second desorbent was used to desorb all of the adsorbed alkanes the monomethyl-branched alkanes would not resolve from the multimethyl-branched alkanes, and the raffinate would contain a mixture of monomethyl-branched alkanes and multimethyl-branched alkanes. On the other hand, if only the first desorbent was used to desorb all of the adsorbed alkanes, the complete desorption of the normal alkanes would require an impracticably high volume of desorbent.

The preferred flowrates of the streams discussed above are as follows. The flowrate of the second desorbent should range between about 2.5 to 12 times that of the feedstock. The flowrate of the second extract stream should be about 90 percent of the second desorbent flowrate. The first desorbent flowrate should be between about 0.8 to about 4 times that of the feedstock. The flowrate of the first extract stream should be controlled so that a majority of monomethyl-branched alkanes are removed in the first extract.

As noted above, the raffinate stream and both extract streams contain a mixture of the separated alkane and desorbent. The multimethyl-branched alkanes in the raffinate stream may be separated from the desorbent and collected. The monomethyl-branched alkanes in the first extract stream may be separated from the desorbent and collected or may be recycled to another unit. Similarly, the normal alkanes in the second extract stream may be separated from the desorbent and recycled to another unit. Desorbent may also be recycled. Of course, in the situation where the desorbent and the separated alkane are identical, no further separation is necessary.

The invention discussed above may also be an integral part of an alkane isomerization process. In this situation, hydrogen and a feedstock containing $C_5$ alkanes along with $C_6$ alkanes and/or $C_7$ alkanes are introduced to an alkane isomerization reactor. It is not necessary that all three classes of alkanes be present in the feedstock; the feedstock could be a mixture of only $C_5$ alkanes and $C_6$ alkanes, or a mixture of only $C_5$ alkanes and $C_7$ alkanes, but for ease of understanding this embodiment of the invention will be discussed as if the feedstock contained a mixture of $C_5$, $C_6$, and $C_7$ alkanes. Most likely the feedstock would contain largely normal and monomethyl-branched alkanes. The specific type of isomerization reactor is not critical and may be of any type commonly known in the isomerization art. Similarly, the isomerization catalyst and operating conditions used are those commonly known in the art, see, for example, Greenough, P.; Rolfe, J. R. K. In *Handbook of Petroleum Refining Processes*; Meyers, R. A., Ed.; McGraw-Hill: New York, 1986; Part 5, pp 5–1 to 5–70. When the feedstock contains $C_7$ alkanes, the catalyst and operating conditions should be chosen to minimize cracking. The effluent of the isomerization reactor would contain a mixture of isomerization products and unisomerized reactants including normal pentane, 2-methylbutane, normal hexane, 2-methylpentane, 3-methylpentane, normal heptane, 2-methylhexane, 3-methylhexane, 2,2-dimethylpropane, 2,3-dimethylbutane, 2,2-dimethylbutane, 2,2-dimethylpentane, 3,3-dimethylpentane, 2,3-dimethylpentane, 2,4-dimethylpentane, 2,2,3-trimethylbutane, and 3-ethylpentane. The multimethyl-branched isomerization products are the valuable alkanes that are to be separated and collected. Monomethyl-branched and normal alkanes may be recycled to the isomerization unit.

The isomerization reactor effluent is passed to a separator where it is fractionated into three portions. 2-Methylbutane is easily fractionated into a first portion and normal pentane is easily fractionated into a second portion. The compounds having the highest boiling points, the $C_6$ and $C_7$ alkanes, are fractionated into a third portion. The 2-methylbutane enriched and the normal pentane enriched portions will be used as the first and second desorbents in a simulated moving adsorbent bed. Therefore, it is not critical for the portions to be pure, but it is important that sufficient 2-methylbutane or normal pentane be present in order for the desorbent to perform as intended. For example, it is not critical that the normal pentane portion be free of 2-methylbutane, but it is important that enough normal pentane be present so that the portion is capable of fully desorbing normal alkanes from an adsorbent. It is preferred that the stream enriched in normal pentane contain at least 50 mass percent normal pentane and the stream enriched in 2-methylbutane contain at least 85 mass percent and most preferred 90 mass percent 2-methylbutane. Because both desorbents needed are generated from the feedstock, it is not necessary to obtain independent sources of desorbents and therefore the overall cost of the process is reduced.

The portion containing the $C_6$ and $C_7$ alkanes is introduced to a simulated moving bed of solid adsorbent particles as the mixture to be separated. The desired components to be separated and collected are the dimethyl-branched $C_6$ alkanes, dimethyl-branched $C_7$ alkanes, trimethyl-branched $C_7$ alkanes, and 3-ethylpentane. Any monomethyl-branched $C_6$ and $C_7$ alkanes, normal hexane, and normal heptane may be recycled to the isomerization reactor. The solid adsorbent particles making up the simulated moving bed are chosen to have selectivity for normal alkanes>monomethyl-branched alkanes>multimethyl-branched alkanes. As the portion containing the $C_6$ and $C_7$ alkanes enters the simulated moving bed and contacts the solid adsorbent particles, the normal alkanes are selectively adsorbed and the monomethyl-branched alkanes are less selectively adsorbed. The adsorbent may be silicalite, ferrierite, zeolite Beta, MAPO-31, SAPO-31, SAPO-11, zeolite X ion exchanged with alkaline cations, alkaline earth cations, or a mixture thereof, or zeolite Y ion exchanged with alkaline cations, alkaline earth cations, or a mixture thereof. The multimethyl-branched alkanes are relatively unadsorbed and are carried with the fluid flow and removed from the simulated moving bed in a raffinate stream. The raffinate stream will contain a mixture of multimethyl-branched alkanes and desorbent. The mixture may be separated, preferably by fractionation, into a multimethyl-branched alkane portion and a desorbent portion. The multimethyl-branched portion may be collected and the desorbent portion may be recycled to the separator discussed above.

The portion containing the 2-methylbutane is introduced to the simulated moving bed as a first desorbent. The 2-methylbutane encounters the solid adsorbent particles containing both monomethyl-branched alkanes and normal alkanes. However, the 2-methylbutane has sufficient desorption capacity to desorb only the monomethyl-branched alkanes that, once desorbed, are removed from the simulated moving bed in a first extract stream. The normal alkanes remain adsorbed in the solid adsorbent particles.

The portion containing the normal pentane is introduced to the simulated moving bed as a second desorbent. The normal pentane encounters the solid adsorbent particles containing the normal alkanes and desorbs the normal alkanes. The desorbed normal alkanes are removed from the simulated moving bed in a second extract zone. The first and second extract streams may be collected or may be recycled to the isomerization reactor for further processing.

Note that if only normal pentane were used as the desorbent for all the adsorbed alkanes, the raffinate would contain both the monomethyl-branched alkanes and the multimethyl-branched alkanes. Normal pentane has such a large desorbent capacity that the monomethyl-branched alkanes and the multimethyl-branched alkanes would not resolve and would co-elute in the raffinate. If only 2-methylbutane, in a practical volume, were used as the desorbent for all the adsorbed alkanes, the normal alkanes would not fully desorb and would build up on the adsorbent. The capacity of the adsorbent would degrade over time, and the adsorbent would need periodic regeneration.

Without intending any limitation on the scope of the present invention and as merely illustrative, this invention is explained below in specific terms as applied to two specific embodiments of the invention. The first embodiment is the separation of a mixture of 23 weight percent 2-methylbutane, 11 weight percent normal pentane, 15 weight percent 2,2-dimethylbutane, 7 weight percent 2,3-dimethylbutane, 21 weight percent 2-methylpentane, 12 weight percent 3 methyl pentane, and 11 weight percent normal hexane and the second embodiment is the continuous isomerization of a mixture of $C_5$, $C_6$, and $C_7$ alkanes including 4 weight percent 2-methylbutane, 8 weight percent normal pentane, 1 weight percent 2,3-dimethylbutane, 2 weight percent 2-methylpentane, 4 weight percent 3-methylpentane, 17 weight percent normal hexane, 42 weight percent normal heptane, 6 weight percent 2-methylhexane, 12 weight percent 3-methylhexane, 1 weight percent 3-ethylpentane, and 3 weight percent 2,3-dimethylpentane to form a mixture of 8 weight percent 2-methylbutane, 4 weight percent normal pentane, 5 weight percent 2,2-dimethylbutane, 3 weight percent 2,3-dimethylbutane, 8 weight percent 2-methylpentane, 5 weight percent 3-methylpentane, 4 weight percent normal hexane, 5 weight percent normal heptane, 11 weight percent 2-methylhexane, 11 weight percent 3-methylhexane, 1 weight percent 3-ethylpentane, 14 weight percent 2,3-dimethylpentane, 9 weight percent 2,2-dimethylpentane, 7 weight percent 2,4-dimethylpentane, 4 weight percent 3,3-dimethylpentane, and 1 weight percent 2,2,3-trimethylbutane using a platinum on tungstated zirconia catalyst. The separation of the desired products is achieved using a simulated moving bed of solid adsorption particles. For ease of understanding, the simulated moving bed of both embodiments of the invention described below is limited to having eight sub-beds.

Referring now to the apparatus as illustrated in FIG. 1, distribution lines 1–8 are available to conduct fluid streams to or from the chamber 10. Chamber 10 houses eight sub-beds of silicalite. The distribution lines connect with the simulated moving bed at locations between successive sub-beds and separate the simulated moving bed into zones as described earlier. The distribution lines 1–8 are also connected to a rotary valve 11. Rotary valve 11 is further connected to: line 12 which conducts the mixture to be separated, described above, to the valve; line 13 which conducts raffinate containing the 2,2-dimethylbutane and the 2,3-dimethylbutane away from the valve; line 14 which conducts the first desorbent, 2-methylbutane, to the valve; line 15 which conducts the first extract, monomethyl-branched alkanes, away from the valve; line 16 which conducts the second desorbent, normal pentane, to the valve; and line 17 which conducts the second extract, normal alkanes, away from the valve. Each of the lines 12–17 is provided with a flow rate sensor and flow control valve (not shown). Line 18 conducts the effluent, or pumparound stream, from the bottom of chamber 10 back to the top of chamber 10 and is equipped with a pump 19.

Using the described apparatus, the invention is performed as follows. The flow rates of each of the lines 12–17 and the step time of rotary valve 11 may be first set to selected values based on the operator's experience. The starting position of the rotary valve is not important; for this illustration the starting position of the rotary valve is such that the normal pentane desorbent is directed to chamber 10 through distribution line 1, the extract containing normal alkanes is directed from chamber 10 through distribution line 2, the 2-methylbutane desorbent is directed to chamber 10 through distribution line 3, the extract containing monomethyl-branched alkanes is directed from chamber 10 through distribution line 4, the mixture to be separated is directed to chamber 10 through distribution line 6, and the raffinate containing multimethyl-branched alkanes is directed from chamber 10 through distribution line 8. When the step time has elapsed, rotary valve 11 advances one index and now directs the normal pentane desorbent through distribution line 2, the extract containing normal alkanes through distribution line 3, the 2-methylbutane desorbent through distribution line 4, the extract containing monomethyl-branched alkanes through distribution line 5, the mixture to be separated through distribution line 7, and the raffinate through distribution line 1. When the step time has again elapsed, the streams will again be directed to the next successive distribution line in the direction of the flow, and the continued progression of the streams will simulate the movement of the solid bed in the countercurrent direction.

For ease of understanding, the operation is described with rotary valve 11 in the starting position as above. When the mixture to be separated, conducted in distribution line 6, enters the simulated moving bed chamber 10 and contacts the silicalite, the multimethyl-branched alkanes, which are relatively unabsorbed by the silicalite, are carried with the fluid flow and withdrawn from the bed in the raffinate stream conducted in distribution line 8. The monomethyl-branched alkanes which are weakly adsorbed by the silicalite and the normal alkanes which are strongly adsorbed by the silicalite are carried with the solid bed in its countercurrent simulated movement thereby being separated from the multimethyl-branched alkanes. The monomethyl-branched alkanes are desorbed by the 2-methylbutane desorbent that is conducted to the bed through distribution line 3. The 2-methylbutane does not have sufficient strength to desorb the normal alkanes that remain adsorbed by the adsorbent. The desorbed monomethyl-branched alkanes are removed from the bed in a first extract stream through distribution line 4. The normal alkanes are desorbed by the normal pentane desorbent that is conducted to the bed through distribution line 1. The desorbed normal alkanes are removed from the bed in a second extract stream through distribution line 2. Note that if normal pentane had been used as the sole desorbent, then the monomethyl-branched alkanes would have been desorbed into the raffinate.

Figure 2:
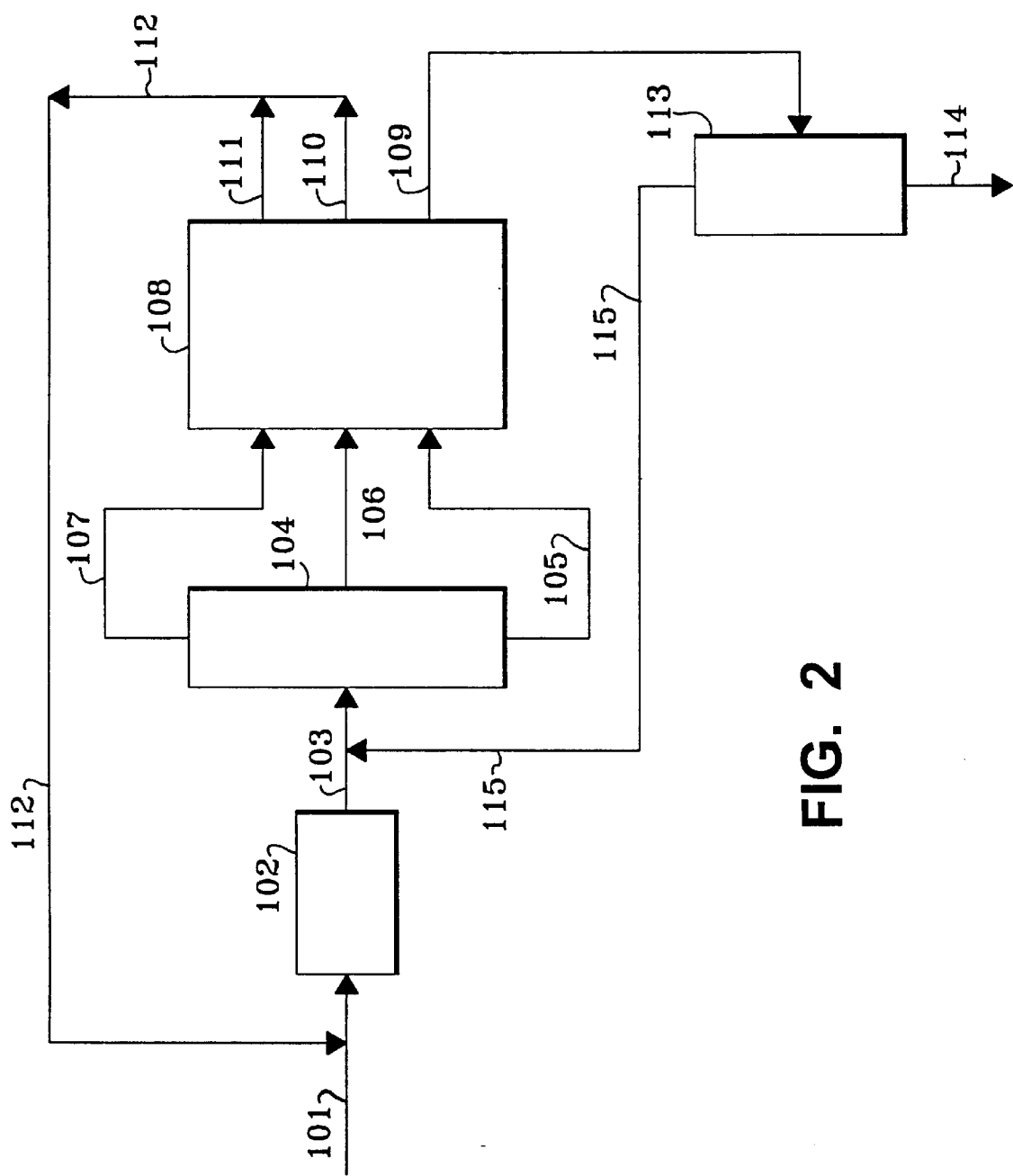
FIG. 2 is a schematic representation of an alkane isomerization process where the mixed isomer reactor effluent is first separated into three portions, each of which is then introduced to a simulated moving bed.

Turning now to FIG. 2, the invention is explained below in terms of the specific embodiment where a $C_5$–$C_7$ naphtha feedstock is isomerized in a fixed bed isomerization reactor, two desorbent streams of different composition and a $C_6$–$C_7$ mixture are generated from the isomerization reactor effluent, and multimethyl-branched alkanes are separated from the $C_6$–$C_7$ mixture using a simulated moving adsorbent bed and the two desorbents. Hydrogen and the $C_5$–$C_7$ naphtha feedstock is conducted in line 101 to the isomerization reactor 102. The isomerization reactor 102 is a fixed bed of 12.5 weight percent tungstate and 0.5 weight percent platinum on zirconia catalyst maintained at 250° C. and 150 psig. In reactor 102 the naphtha feedstock is isomerized to form an effluent containing near equilibrium concentrations of normal $C_5$–$C_7$ alkanes, monomethyl-branched $C_5$–$C_7$ alkanes, and multimethyl-branched $C_6$–$C_7$ alkanes which are conducted from isomerization reactor 102 in line 103. It is possible that some 2,2-propane may be formed in isomerization reactor 102 but it is unlikely to be formed in any appreciable quantity and therefore will not be discussed here. Should 2,2-propane be formed, it may be easily removed so as to prevent buildup by commonly known techniques such as a purge stream. Excess hydrogen is removed from the effluent and may be recycled (not shown).

The effluent in line 103 is conducted to separator 104 which is a 100 equilibrium stage fractionation column operating at 30 psia and temperatures of 52° C. at the top, 88° C. at the bottom, and 56° C. where the sidecut is withdrawn. The portion with the highest boiling point materials, the $C_6$–$C_7$ alkanes, is easily fractionated into line 105. The $C_5$ alkanes are fractionated into a portion containing 85 mass percent 2-methylbutane conducted in line 107 and a portion containing 50 mass percent normal pentane conducted in line 106. All three portions are conducted to simulated moving bed separation zone 108 containing silicalite with the $C_6$–$C_7$ portion being the mixture to be separated, the 2-methylbutane portion being the first desorbent, and the normal pentane portion being the second desorbent.

The apparatus and operation of simulated moving bed separation zone 108 is described in detail above in reference to FIG. 1. The separated monomethyl-branched alkanes and normal alkanes are conducted from the zone in lines 110 and 111, respectively, and are combined to form line 112 and recycled to combine with the feedstock in line 101. Multimethyl-branched alkanes, in a mixture with desorbent, are conducted from the zone in line 109 to 25 equilibrium stage fractionator 113 operating at 30 psig and temperatures of 52° C. at the top and 88° C. at the bottom, wherein the desorbent is fractionated from the multimethyl-branched alkanes. The desorbent is recycled in line 115 to combine with reactor effluent in line 103, and the multimethyl-branched alkanes are collected from line 114.

It must be emphasized that the above descriptions are merely illustrative of preferred embodiments and are not intended as undue limitations on the generally broad scope of the invention. Moreover, while the descriptions are narrow in scope, one skilled in the art will understand how to extrapolate to the broader scope of the invention. For example, operation of the invention where the sub-beds of the simulated moving bed may be housed in two or more interconnected chambers can be readily extrapolated from the foregoing description. Similarly, one skilled in the art would understand that the desorbents and the mixture to be separated may have different compositions. Furthermore, the optimum number of sub-beds, the optimum cycle time, and the optimum flow rates would be readily determined by one skilled in the art.

EXAMPLE

Two pulse tests were performed demonstrating the differing desorbent capacity of normal pentane and 2-methylbutane in combination with silicalite adsorbent. In each pulse test, a fixed bed column was packed with silicalite and held at 200° C. and 70 psig. Desorbent was flowed through the bed, and at a specific time a 1 cc pulse of feedstock containing different alkane isomers was introduced to the column. The effluent was analyzed by gas chromatography and the results are listed in Tables 1 and 2.

TABLE 1

| Component | Retention Volume with normal pentane desorbent (cc) | Retention Volume with 2-methylbutane desorbent (cc) |
| --- | --- | --- |
| 2,2-dimethylbutane | 0 | 0 |
| 2,3-dimethylbutane | 0 | 1 |
| 2-methylpentane | 4 | 8 |
| normal hexane | 13 | 20 |

TABLE 2

| Component | Retention Volume with normal pentane desorbent (cc) | Retention Volume with 2-methylbutane desorbent (cc) |
| --- | --- | --- |
| 2,2,3-trimethylbutane | 0 | 0 |
| 2,2-dimethylpentane | 2 | 0 |
| 2,4-dimethylpentane | 1 | 1 |
| 2-methylhexane | 7 | 33 |
| normal heptane | 24 | 65 |

What is claimed is:

1. A process for separating multimethyl-branched alkanes from a mixture of multimethyl-branched alkanes, monomethyl-branched alkanes, and normal alkanes into a stream enriched in multimethyl-branched alkanes, a stream enriched in monomethyl-branched alkanes, and a stream enriched in normal alkanes comprising:

a) introducing the mixture to a simulated moving bed of solid adsorbent particles selected from the group consisting of silicalite, ferrierite, zeolite Beta, MAPO-31, SAPO-31, SAPO-11, zeolite X ion exchanged with alkaline cations, alkaline earth cations, or a mixture thereof, and zeolite Y ion exchanged with alkaline cations, alkaline earth cations, or a mixture thereof, said particles having the selectivity normal alkanes>monomethyl-branched alkanes>multimethyl-branched alkanes;

b) removing and collecting a raffinate stream enriched in multimethyl-branched alkanes;

c) desorbing the monomethyl-branched alkanes using a first desorbent capable of desorbing the monomethyl-branched alkanes but incapable of desorbing the normal alkanes;

d) removing and collecting a first extract stream enriched in monomethyl branched alkanes;

e) desorbing the normal alkanes using a second desorbent; and f) removing and collecting a second extract stream enriched in normal alkanes.

2. The process of claim 1 where the first desorbent is a mixture of alkanes having 4 to 5 carbon atoms and containing largely 2-methylbutane, isobutane, normal butane, or a combination thereof.

3. The process of claim 1 where the second desorbent is a mixture of alkanes having 4 to 5 carbon atoms and containing largely normal pentane.

4. The process of claim 2 where the first desorbent contains at least 85 mass percent 2-methylbutane.

5. The process of claim 3 where the second desorbent contains at least 60 mass percent normal pentane.

6. The process of claim 1 where the mixture of alkanes comprises $C_6$ alkanes, $C_7$ alkanes, or a combination thereof.

7. A process for producing and separating multimethyl-branched alkanes from a feedstock containing $C_5$ alkanes along with $C_6$ alkanes, $C_7$ alkanes, or a combination thereof, said process comprising:

a) catalytically isomerizing, in the presence of hydrogen, the feedstock to form a mixture of normal, monomethyl-branched, and multimethyl-branched alkanes;

b) separating the mixture into at least three portions:
  i) a portion enriched in 2-methylbutane,
  ii) a portion enriched in normal pentane,
  iii) a portion enriched in alkanes having 6 or more carbon atoms;

c) introducing the portion enriched in alkanes having 6 or more carbon atoms to a simulated moving bed of solid adsorbent particles selected from the group consisting of silicalite, ferrierite, zeolite Beta, MAPO-31, SAPO-31, SAPO-11, zeolite X ion exchanged with alkaline cations, alkaline earth cations, or a mixture thereof, and zeolite Y ion exchanged with alkaline cations, alkaline earth cations, or a mixture thereof, said particles having the selectivity normal alkanes>monomethyl-branched alkanes>multimethyl-branched alkanes;

d) removing and collecting a raffinate stream enriched in multimethyl-branched alkanes;

e) desorbing the monomethyl-branched alkanes using the portion enriched in 2-methylbutane;

f) removing and collecting a first extract stream enriched in monomethyl-branched alkanes;

g) desorbing the normal alkanes using the portion enriched in normal pentane; and h) removing and collecting a second extract stream enriched in normal alkanes.

8. The process of claim 7 further comprising recycling the first and second extract streams to combine with the feedstock.

9. The process of claim 7 further comprising separating 2-methylbutane and normal pentane from the raffinate stream.

10. The process of claim 9 further comprising recycling the separated 2-methylbutane and normal pentane to (b) of claim 7.

11. The process of claim 7 where the portion enriched in 2-methylbutane contains at least 85 mass percent 2-methylbutane.

12. The process of claim 7 where the portion enriched in normal pentane contains at least 60 mass percent normal pentane.

* * * * *